United States Patent [19]

Genese et al.

[11] 4,372,306
[45] Feb. 8, 1983

[54] EQUIPMENT SETS HAVING A COMBINED AIR BARRIER AND LIQUID SEQUENCING DEVICE FOR THE SEQUENTIAL ADMINISTRATION OF MEDICAL LIQUIDS AT DUAL FLOW RATES

[75] Inventors: Joseph N. Genese, Waukegan; Andrew J. Muetterties, Mundelein, both of Ill.

[73] Assignee: Abbott Laboratories, North Chicago, Ill.

[21] Appl. No.: 228,632

[22] Filed: Jan. 26, 1981

Related U.S. Application Data

[63] Continuation-in-part of Ser. No. 16,461, Feb. 28, 1979, Pat. No. 4,256,104, Ser. No. 157,922, Jun. 9, 1980, Pat. No. 4,324,238, and Ser. No. 167,948, Jul. 14, 1980, Pat. No. 4,316,460.

[51] Int. Cl.³ .............................................. A61M 5/14
[52] U.S. Cl. ............................... 128/214 G; 128/227; 137/113; 222/145
[58] Field of Search ............ 128/214 R, 214 G, 214.2, 128/227; 137/173, 183, 198, 199, 113; 55/159; 222/145

[56] References Cited

U.S. PATENT DOCUMENTS

| | | | |
|---|---|---|---|
| 3,886,937 | 6/1975 | Bobo et al. | 128/214 R |
| 4,005,710 | 2/1977 | Zeddies et al. | 128/214 R |
| 4,105,029 | 8/1978 | Virag | 128/214 R |
| 4,116,646 | 9/1978 | Edwards | 55/159 |
| 4,223,695 | 9/1980 | Muetterties | 128/214 G X |
| 4,316,460 | 2/1982 | Genese et al. | 128/214 R |
| 4,324,238 | 4/1982 | Genese et al. | 128/214 G |

FOREIGN PATENT DOCUMENTS 2059776  4/1981  United Kingdom ........... 128/214 G

OTHER PUBLICATIONS

Page 12 of Abbott Labs. catalog "Sets for Dual Containers".

Primary Examiner—Dalton L. Truluck
Attorney, Agent, or Firm—Robert S. Beiser; Robert L. Niblack

[57] ABSTRACT

Equipment sets for the sequential administration of medical liquids allow primary liquid to be administered at a flow rate independent of the flow rate of a secondary liquid. The sets include a combined air barrier and liquid sequencing device to prevent the inadvertent administration of air when secondary liquid is depleted. The device also prevents the flow of primary liquid when secondary liquid is being dispensed.

11 Claims, 12 Drawing Figures

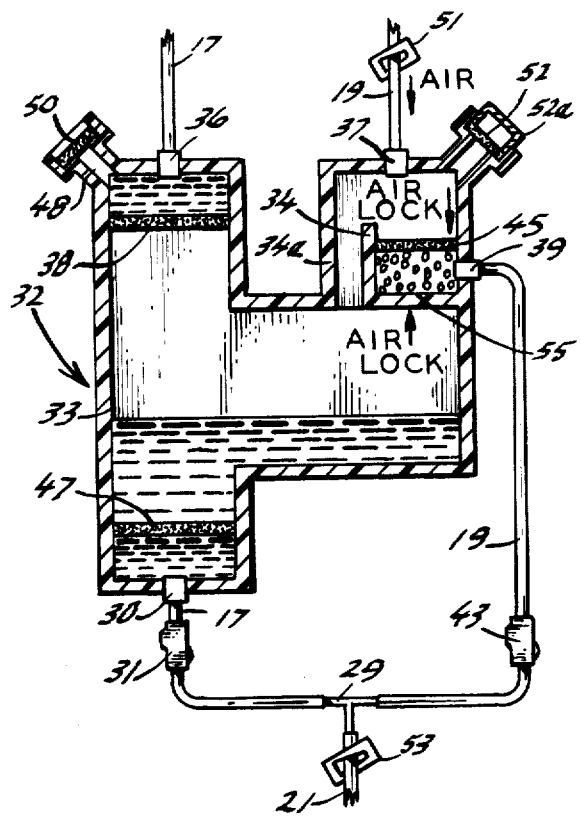
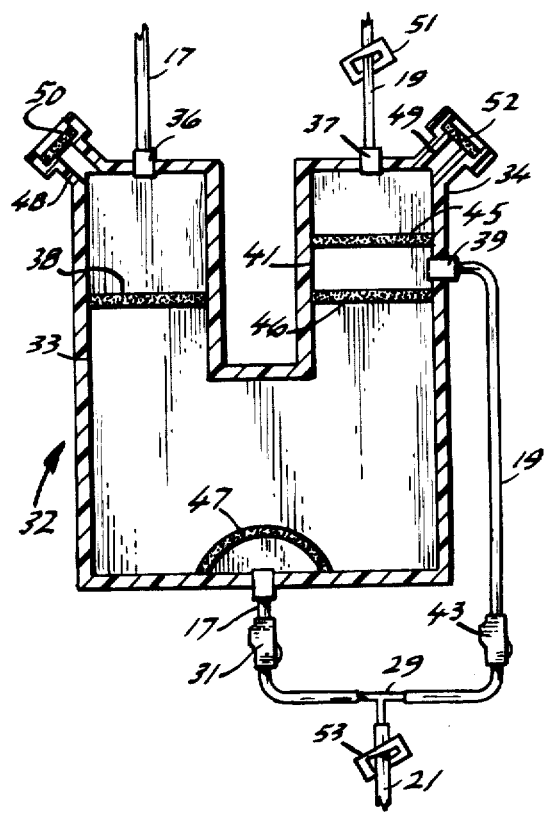
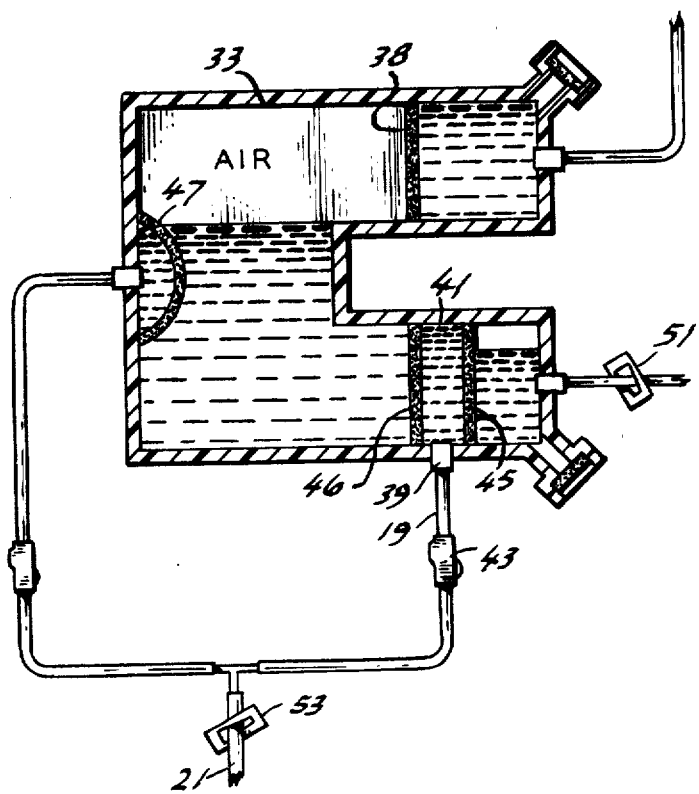

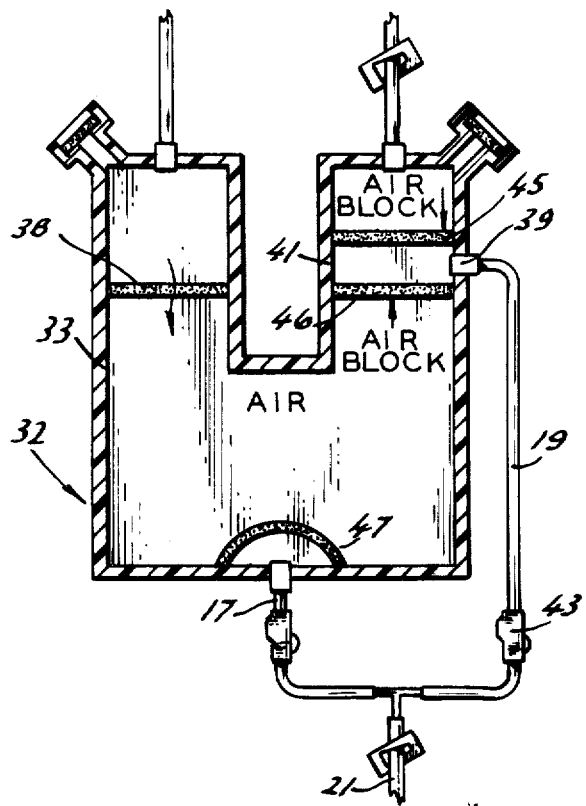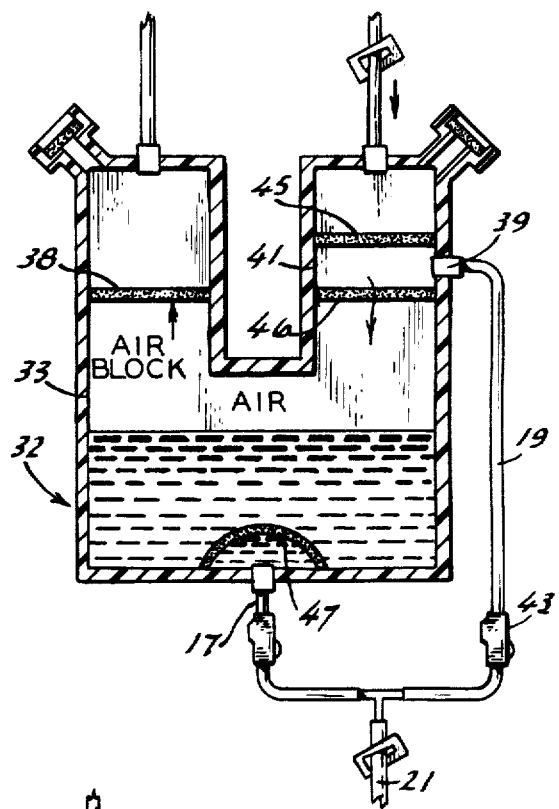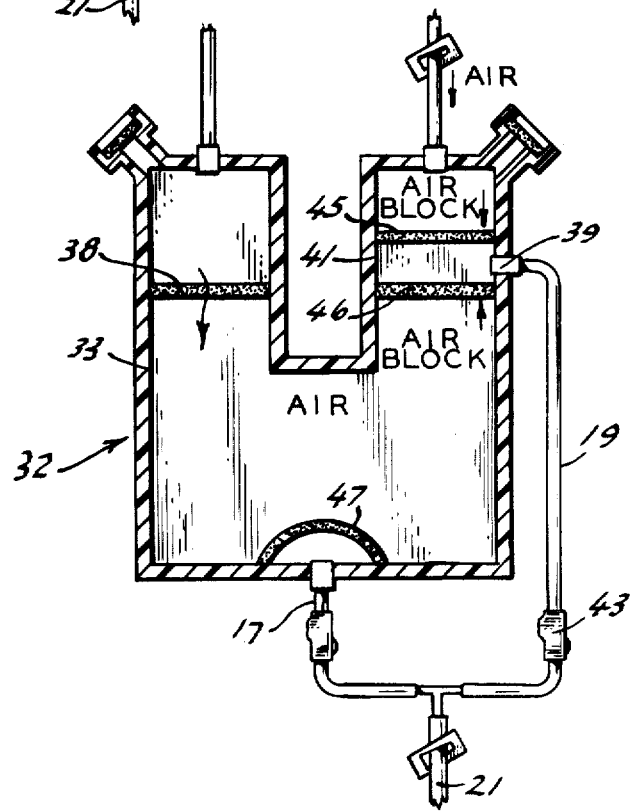

EQUIPMENT SETS HAVING A COMBINED AIR BARRIER AND LIQUID SEQUENCING DEVICE FOR THE SEQUENTIAL ADMINISTRATION OF MEDICAL LIQUIDS AT DUAL FLOW RATES

BACKGROUND OF THE INVENTION

This application is a continuation-in-part of U.S. patent application Ser. No. 16,461 filed Feb. 28, 1979 now U.S. Pat. No. 4,256,104, Ser. No. 157,922 filed June 9, 1980 and 167,948 filed July 14, 1980 now U.S. Pat. Nos. 4,324,238 and 4,316,460 respectively.

The present invention relates to systems and equipment sets for the administration of medical liquids to a patient, and more particularly, to systems and equipment sets for the sequential administration of a plurality of medical liquids.

The parenteral administration of medical liquids to patients is a long established practice. Liquids including amino acids, blood, dextrose, electrolytes, and saline are commonly administered to patients over prolonged periods of time. Generally, these liquids are administered from a glass bottle or plastic bag suspended above the patient and containing 250–2,000 ml. of the liquid. Such prolonged infusions commonly are administered at a flow rate of 10–150 ml./hr.

Frequently, the patient must receive an additional or secondary liquid while the prolonged infusion is being administered. Preferably, this secondary liquid should be administered through the same hypodermic needle to avoid the unnecessary pain and trauma to the patient of additional venipunctures. To avoid dilution and incompatability problems, it is also preferable that the primary flow be temporarily interrupted, the secondary liquid administered and the flow of the primary liquid resumed. Generally, the secondary liquid will be administered at a flow rate of 50–250 ml./hr.

Abbott Laboratories, North Chicago, Illinois manufactures a Y-type set for the sequential administration of primary and secondary liquids. These VENOSET® piggyback sets allow the prolonged infusion of a primary liquid to be temporarily halted by means of a backcheck valve in the primary liquid flow path in order to administer a secondary liquid without the need for a new venipuncture. Then, when the secondary liquid has been depleted, the backcheck valve automatically opens to resume flow of the primary liquid. An important characteristic of this system is that the secondary liquid container must be suspended at a higher height than the primary liquid container to establish the liquid pressure differential that closes the backcheck valve in the primary liquid flow path.

A similar system is disclosed in U.S. Pat. No. 3,886,937 granted June 3, 1975 to D. Bobo, et al., assigned to American Hospital Supply Corp., and entitled "Medical Administration Set for Dispensing Plural Medical Liquids". Another similar system is disclosed in U.S. Pat. No. 4,105,029 granted Aug. 8, 1978 to R. Virag, assigned to Baxter Travenol Laboratories, Inc. and entitled "Intravenous Solution Sets Having an Air Access Site and Constricted Inner Diameter Portion". Float type valves for such systems are illustrated by U.S. Pat. No. 4,176,558 granted Nov. 27, 1979 and assigned to Baxter Travenol Laboratories, Inc.

An inherent disadvantage of all of the above-mentioned prior art medical liquid administration systems is that they each resume the flow of primary liquid at the rate the secondary liquid had been flowing. Because the preferred flow rate of the secondary liquid is generally greater than the preferred flow rate of the primary liquid, when the primary liquid resumes flow at that rate, the patient can be administered an excessive amount of primary liquid, unless the flow rate of the primary liquid is adjusted to the preferred primary flow rate soon after the flow of primary liquid resumes.

A remedy to the above-described disadvantage would appear to be provided by simply incorporating flow control devices into both the primary and secondary liquid flow paths. However, while this remedy does provide dual flow rates for the primary and secondary liquids, it is unacceptable. That is, because the common tube of the Y-set must be able to accommodate both flow rates, when the primary liquid is flowing at a slower rate than the secondary liquid was, there will be an unfilled volume or void in the common tube. To fill that void, air will be drawn into the common tube from the depleted secondary container. That air will then be driven into the patient by the weight of the primary liquid, thereby causing a serious embolism and perhaps, the patient's death.

Accordingly, it will be apparent that an efficacious system for the sequential administration of medical liquids at dual flow rates would be advantageous to the medical profession.

SUMMARY OF THE INVENTION

The primary advantage of the present invention, therefore, is to provide a system for the sequential administration of medical liquids at dual flow rates that will not draw air from the secondary container when the secondary liquid has been depleted. Another advantage is to provide equipment sets that embody the system of this invention.

In accordance with these and other advantages, there is provided by the present invention a gravitational flow system for the sequential administration of medical liquids to a patient which includes a primary liquid container, a primary tube, a secondary liquid container, a secondary tube, and a common tube all connected in fluid communication to form a primary liquid flow path and a secondary liquid flow path. The primary liquid flow path includes the primary and common tube, while the secondary liquid flow path includes the secondary and common tubes. A primary flow control is provided on the primary tube for adjusting the flow rate of the primary liquid to a rate independent of the flow rate of the secondary liquid. Similarly, a secondary flow control in the secondary liquid flow path for adjusting the flow rate of the secondary liquid is provided.

The primary tube includes a primary valve which allows primary liquid to flow from the primary container whenever the height of primary liquid is greater than or equal to the height of the secondary liquid in the system. The primary valve also prevents primary liquid from flowing out of the primary container whenever the height of the primary liquid is less than the height of the secondary liquid in the system. An air barrier in the secondary liquid flow path which is substantially impervious to air is provided to insure that air is not drawn from the secondary container when the secondary liquid is depleted. The air barrier and primary valve in the present invention are housed in a combined air barrier and liquid sequencing valve.

The combined air barrier and liquid sequencing valve is divided into two chambers, with the first chamber having an inlet port for primary liquid and an outlet port with a hydrophilic membrane incorporated therein, which prevents the passage of air from the first chamber, but allows the passage of liquid. The valve also has a second chamber which admits secondary liquid through an inlet port and which dispenses secondary liquid through an outlet port. This outlet port also has a hydrophilic membrane to prevent the passage of air. An air capturing pocket positioned beneath the inlet to the first chamber traps residual air during administration of secondary liquid, causing primary liquid flow to cease until the secondary liquid is depleted. Primary liquid flow then automatically resumes.

BRIEF DESCRIPTION OF THE DRAWING

Other objects and attendant advantages will become obvious to those skilled in the art by reading the following detailed description in connection with the accompanying drawing, wherein like reference characters designate like or corresponding parts throughout the several figures thereof and wherein:

FIGS. 3–7 are vertical sections of the combined air barrier and liquid sequencing valve of FIG. 2.

FIGS. 8–12 are vertical sections of an alternative version of the combined air barrier and liquid sequencing valve of FIG. 1.

DETAILED DESCRIPTION OF THE INVENTION

Figure 1:
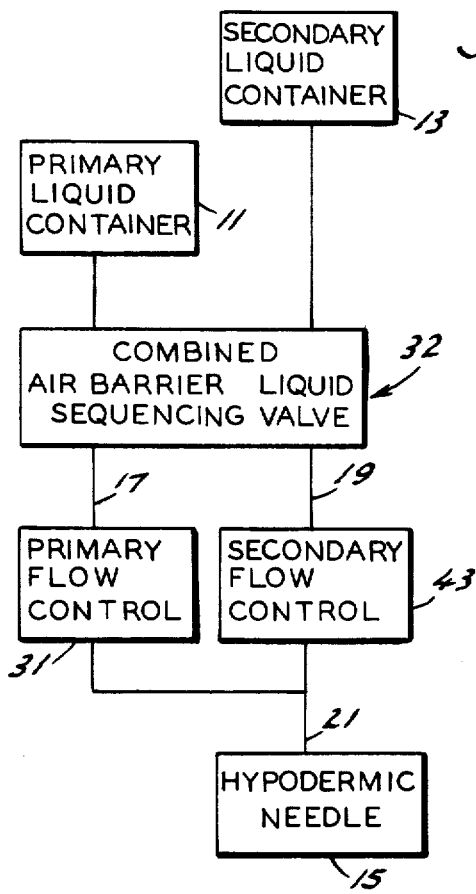
FIG. 1 is a schematic block diagram of the efficacious system for the sequential administration of medical liquids at dual flow rates contemplated by this invention.

Referring to the drawing, there is shown in FIG. 1, a schematic block diagram of the basic elements of a gravitational flow system for the sequential administration of medical liquids at dual flow rates contemplated by this invention.

The diagram depicts a primary liquid container 11 that contains a primary medical liquid to be administered to a patient for a prolonged period of time. The diagram also depicts a secondary liquid container 13 that contains a secondary medical liquid to be administered to the patient, usually for a relatively short period of time, during which time the administration of the primary liquid will be temporarily interrupted. Containers 11 and 13 can be glass bottles, plastic flexible bags, or any other suitable container. Primary container 11 and secondary container 13 are connected in fluid communication to a conventional hypodermic needle 15 through a primary tube 17, a secondary tube 19, and a common tube 21. Thus, the primary liquid flow path from primary container 11 to needle 15 comprises primary tube 17 and common tube 21. Likewise, the secondary liquid flow path from secondary container 13 to needle 15 comprises secondary tube 19 and common tube 21.

Figure 2:
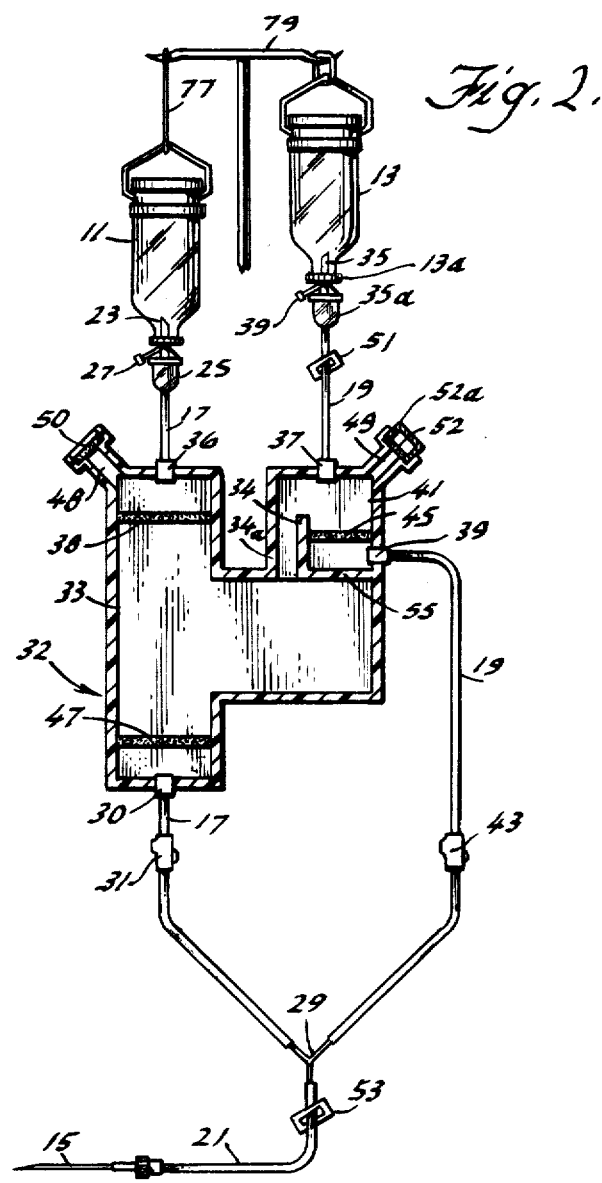
FIG. 2 is a front view partially in cross section of the equipment set of FIG. 1 employing one embodiment of a combined air barrier and liquid sequencing valve.

As best seen in FIG. 2, the distal end of primary tube 17 is in fluid communication with primary container 11, preferably by means of a piercing pin 23 inserted into a puncturable closure of container 11. Piercing pin 23 can have an integral drip chamber 25, and when container 11 is a glass bottle, as shown in the set of FIG. 2, an integral filtered air vent 27. Such piercing pins, drip chambers and air vents are well known in the medical practice and need not be more fully explained here.

The proximal end of primary tube 17 is joined in fluid communication to the distal end of common tube 21, preferably by a Y-tube 29, it being understood that the primary, secondary and common legs of Y-tube 29 constitute a portion of the primary, secondary and common tubes 17, 19 and 21, respectively. Primary tube 17 has a primary flow control 31 at any convenient location intermediate its ends for independently adjusting the rate of flow of the primary liquid through the primary liquid flow path. Preferably, as shown in FIG. 2, primary flow control 31 can be a roller clamp. However, it can be any other adjustable device that will reliably maintain a desired primary liquid flow rate.

The distal end of secondary tube 19 is in fluid communication with secondary container 13, preferably, by means of a piercing pin 35 inserted into a puncturable closure 13a of container 13. Piercing pin 35 can have an integral drip chamber 35a, and when container 13 is a glass bottle, as shown in FIG. 2, an integral, filtered air vent 39. The proximal end of secondary tube 19 is joined in fluid communication to the distal end of common tube 21, preferably, by a Y-tube 29. A secondary flow control 43 is disposed at any convenient location in the secondary liquid flow path. Preferably, secondary flow control 43 can be a roller clamp. However, it can be any other adjustable device that can reliably maintain a desired secondary liquid flow rate.

A combined air barrier and liquid sequencing valve comprising a housing 32 is shown in FIG. 1. Housing 32 has first chamber 33 and second chamber 41, as shown in FIGS. 2–11. First and second chambers 33 and 41 each have inlet and outlet ports thereto through housing 32 that are respectively connected in fluid communication to the other portions of the primary or secondary tubes 17 and 19. Primary tube 17 thus includes first chamber 33 of housing 32, while secondary tube 19 includes second chamber 41.

First chamber 33 has valve means associated with its ports that allow primary liquid to flow from primary container 11 whenever the height of the primary liquid is greater than or equal to the height of the secondary liquid in the system of FIG. 1. Further, the valve means associated with first chamber 33 prevents the flow of primary liquid from primary container 11 whenever the height of the primary liquid is less than the height of the secondary liquid in the system.

As shown in FIG. 2 and more fully explained in the following explanation of the operation of the sets of this invention, the valve means associated with first chamber 33 is a hydrophilic membrane 38 which covers inlet port 36 at the top of first chamber 33. Outlet port 30 is preferably located at the bottom of first chamber 33. It will be readily apparent that various other valves can be provided to inlet 36 or outlet 30 of first chamber 33.

Second chamber 41 of combined air barrier and liquid sequencing valve housing 32 as shown in FIGS. 2–6 preferably has an inlet port 37 at its top and an outlet port 39 at its side. Second chamber 41 has means associated with outlet port 39 that are substantially impervious to air while the set is in use and prevent the flow of air through the secondary flow path. In particular, as shown in FIG. 2, the outlet 39 from second chamber 41 is sealed by a hydrophilic membrane filter 45. Hydrophilic membranes 38 and 45 are impermeable to air when wet, which they are during the use of the sets of this invention. The hydrophilic filters can be formed from material such as cellulose acetate material produced by the Millipore Filter Corporation of Bedford, Massachusetts or the Sartorius-Membranfilter GmbH of Weender Landstr, West Germany.

The housing 32 of the set shown in FIGS. 2-7 includes air vent tubes 48 and 49 and filtered openings 50 and 52. Alternatively, openings 50 and 52 can be filtered by a hydrophobic membrane filter which is permeable by air, but not liquids. The hydrophobic filters can be formed of polyfluorotetraethylene, hexafluoropropylene/tetrafluoroethylene copolymer, or other suitable materials. One such filter is made of Gelman ANH-450 material made by Gelman Instruments of Ann Arbor, Michigan. In the embodiment shown in FIGS. 2-7, opening 52 is sealed by cap 52a.

As shown in FIG. 2, second chamber 41 has a reservoir 55 for liquid which has an open top located directly under the opening to second chamber 41. Preferably, vertical wall 34 can be an integral part of reservoir 55.

Alternatively, as seen in FIGS. 8-12, reservoir 55 may be replaced by a second hydrophilic membrane 46 located below membrane 45 to direct a portion of secondary liquid into secondary tube 19. In all the embodiments shown, a third hydrophilic membrane 47 prevents passage of air through primary tube 17.

For simplicity, the equipment sets embodying the combined air barrier and liquid sequencing valve of FIGS. 2-11 have been depicted and described as an integral unit of FIGS. 1 and 2. It is apparent, however, that the sets can be manufactured and assembled in subsets and that each subset will accordingly be provided such resealable closures, piercing means, adapters, etc. as are necessary to permit their easy assemblage into the complete set at an appropriate time. It will also be apparent that some of the several components of the air barrier and liquid sequencing valve of FIGS. 2-11 can be interchanged or combined in combinations other than those specifically depicted.

Operation of the System

As depicted in FIGS. 1 and 2, primary container 11 is suspended in space at a height above the patient by means of a hook 77 and stand 79. It will be apparent that other means for suspending the containers of this invention are well known.

To insure that all the air that might be forced into the patient has been removed from the set, the set is initially primed by first closing all slide clamps 51 and 53, if present. Piercing pin 23 is then inserted into the resealable closure of primary container 11. In the set of FIGS. 2-7, secondary flow control 43 is fully opened. Primary liquid is then allowed to fill housing 32 and secondary tube 19 up to slide clamp 53. Primary flow control 31 and slide clamp 53 are then opened to allow primary liquid to flow through the primary liquid flow path and force all the air therefrom that might be forced into the patient. Slide clamp 53 is then closed.

In the sets of FIGS. 2-7, air will pass through hydrophilic membrane 38 initially until the primary liquid fills first chamber 33 and then wets hydrophilic membrane 38 as it passes through it. Then air will no longer pass through membrane 38.

In the sets of FIGS. 8-12, combined air barrier and liquid sequencing valve 32 is tilted (FIG. 9) and secondary flow control 43 is then opened to allow primary liquid to flow into, or back-prime, secondary flow path 19 until the liquid is above and forces all the air therein above the outlet through second chamber 41 and into first chamber 33. Slide clamp 49 is then closed. Primary liquid will flow into, or back-prime, secondary flow path 19 until liquid reaches and wets hydrophilic membranes 45 and 46, which can then no longer vent air, thereby preventing the further flow of air into secondary tube 19. A substantial volume of air will remain in first chamber 33. Alternatively, slide clamp 51 can be opened to allow secondary liquid to force air out of the entire secondary tube 19. Slide clamp 51 is then closed, and housing returned to a vertical position.

Figures 3, 5:
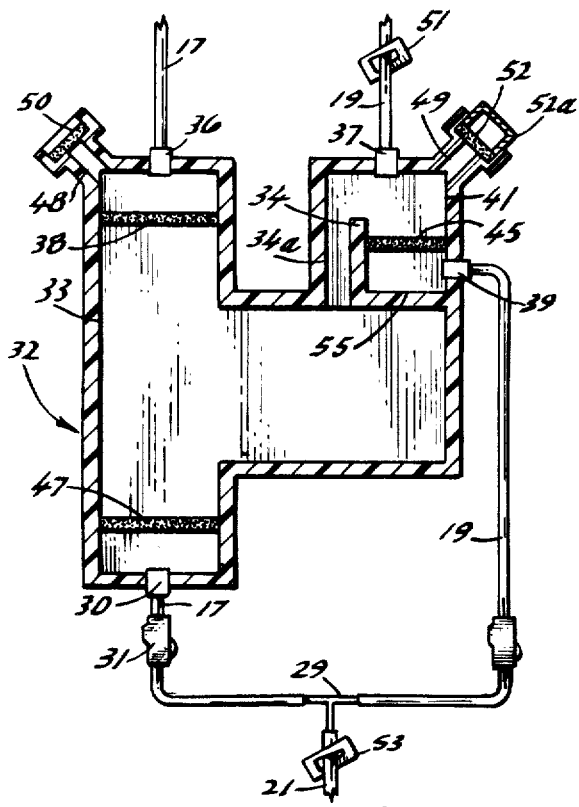

Common tube 21 has a Y adapter at its proximal end open to the flow of liquid therefrom, is connected to needle 15, which will generally have been already inserted into a vein of the patient. Primary flow control 31 is next adjusted to a setting that will provide the desired flow rate for a prolonged infusion of primary liquid into the patient, generally 10-150 ml./hr. As is well known in the medical practice, that flow rate can be visually observed by viewing and counting drops passing through the primary drip chamber 25. As seen in FIGS. 5 and 10, primary liquid will then be administered, with hydrophilic membrane 45 preventing the passage of any residual air through port 39.

When it is desired to administer a secondary liquid to a patient using the sets of FIGS. 2-7, piercing pin 35 of secondary tube 19 is inserted into the resealable closure 13a of secondary container 13. If the portion of secondary tube 19 above the inlet port 37 to second chamber 41 is detachable, it can then be detached and slide clamp 51 opened to force the air from that portion of tube 19. Slide clamp 51 is then closed and the tubing attached to the inlet port to second chamber 41. Secondary container 13 is then suspended in space at a height substantially greater than the height of primary container 11. The set will now be in the mode illustrated in FIG. 2.

Figures 4, 6:
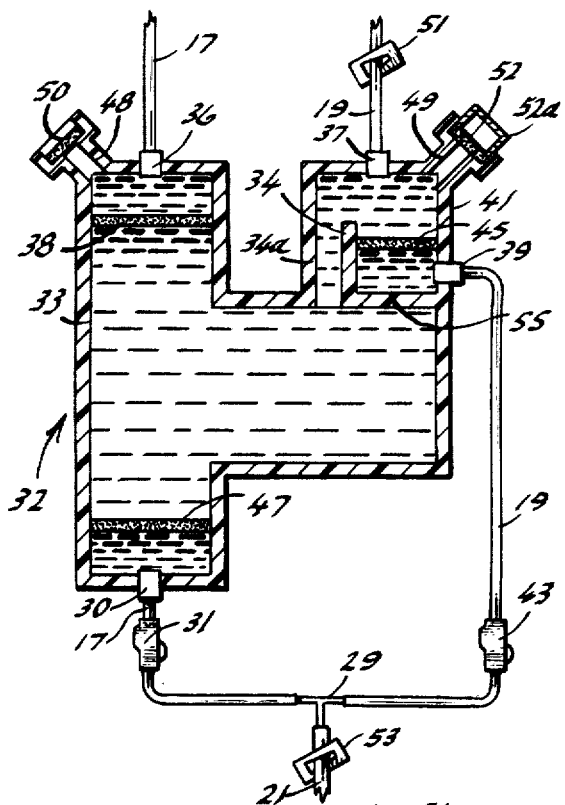

As seen in FIG. 6, when slide clamp 51 is opened, secondary liquid will then immediately begin to flow into reservoir 55 of second chamber 41. Because hydrophilic membrane 45 was wetted during the initial priming of the set, and vent 52 is sealed by cap 52a, air can only escape from second chamber 41 through the aperture 34a in vertical wall 34 into first chamber 33. Thus, as secondary liquid enters reservoir 55, the air it displaces will be forced into first chamber 33 by the pressure of the secondary liquid.

Because hydrophilic membrane 38 is wet, air in first chamber 33 cannot pass through it. Therefore, as the pressure of secondary liquid entering reservoir 55 continues to force air into first chamber 33, that air will accumulate along the top wall of chamber 33. Because the pressure of secondary liquid forcing the air into chamber 33 is greater than the pressure of primary liquid contacting the air, the air will displace the primary liquid in first chamber 33.

The displaced primary liquid is retarded from entering inlet 36 of first chamber 33. Thus, hydrophilic membrane 38 and the air displaced from second chamber 41 block the flow of primary liquid from primary container 11 through the primary liquid flow path as long as the height of secondary liquid in the system is greater than that of the primary liquid.

As further shown in FIG. 6, once reservoir 55 becomes filled with secondary liquid, it will pass out of second chamber 41 through its outlet port 39 into first chamber 33 and also overflow reservoir 55. Secondary flow control 43 is then adjusted to a desired flow rate, typically 50-250 ml./hr. for the secondary liquid, which will then flow until the liquid in secondary container 13 is depleted. The flow of secondary liquid through outlet 30 is also included in calculating total flow. It will be apparent that the initial liquid flowing from secondary tube 19 will be the liquid with which it was primed.

As seen in the system of FIGS. 8-12 and in particular FIG. 11, when secondary liquid flows into second chamber 41 through membrane 45, a portion of the secondary liquid will pass out of port 39 and a portion will pass through membrane 46. The pressure of this liquid will force air into first chamber 33 and will block primary flow as described above.

When the height of primary liquid in the system of FIG. 1 as depicted in the sets of FIG. 12 becomes greater than the height of the secondary liquid, the valve means associated with the ports of first chamber 33 will immediately allow primary liquid to flow from the primary container at the flow rate to which primary flow control 31 is adjusted. As seen in FIGS. 7 and 12, because the pressure of the primary liquid pushing on the air at the top of first chamber 33 is now greater than that of the secondary liquid, the primary liquid forces the air back into second chamber 41, thereby unlocking the "air lock" that had prevented primary liquid from flowing out of first chamber 33.

The primary flow rate is independent of the secondary flow rate. In those instances where it is less than or equal to the secondary flow rate, both primary and secondary liquid will flow through common tube 21, until air reaches the air barrier in second chamber 41. Then only primary liquid will enter common tube 21. The air barrier in second chamber 41 then prevents air from being drawn into common tube 21 and eventually to the patient's vein.

When primary container 11 becomes depleted of primary liquid, the primary piercing pin 23 is merely removed therefrom and inserted into the resealable closure of a new primary container, which is then suspended in place of the previous container. When secondary container 13 becomes depleted of secondary liquid, it can be left empty until another secondary liquid is to be administered. When another secondary liquid is to be administered, the secondary piercing pin 35 is merely removed from secondary container 13 and inserted into a new secondary liquid container. The combined air barrier and liquid sequencing valve is then briefly inverted to spill any liquid from reservoir 55 remaining therein and the procedure used for initiating the flow of secondary liquid from the first secondary container is repeated.

Having described the invention in specific detail and exemplified the manner in which it may be carried into practice, it will now be readily apparent to those skilled in the art that innumerable variations, applications, modifications and extensions of the basic principles involved may be made without departing from its sphere or scope.

We claim:

1. A gravitational flow system for the sequential administration of medical liquids to a patient comprising:
a primary container suspended in space for containing a primary medical liquid;
a primary tube having its distal end in fluid communication with said primary container;
a secondary container suspended in space at a height greater than that of said primary container for containing a secondary medical liquid;
a secondary tube having its distal end in fluid communication with said secondary container;
a common tube having its distal end in fluid communication with the proximal ends of said primary and secondary tubes and its proximal end open for the flow of liquid therethrough to form a primary liquid path comprising said primary tube and said common tube and a secondary liquid flow path comprising said secondary tube and said common tube;
secondary flow control means in said secondary liquid flow path for adjusting the flow rate of said secondary liquid therethrough;
primary flow control means on said primary tube for adjusting the flow of said primary liquid through said primary liquid flow path at a rate independent of the flow rate of said secondary liquid through said secondary liquid flow path;
a combined air barrier and liquid sequencing valve interposed in said primary and secondary flow paths which allows primary liquid to flow from said primary container whenever the height of said primary liquid is greater than or equal to the height of said secondary liquid in said system and which prevents primary liquid from flowing from said primary container whenever the height of said primary liquid is less than the height of said secondary liquid in said system;
said combined air barrier and liquid sequencing valve comprising a housing divided into two or more parallel chambers, at the top thereof a first chamber in said housing having an inlet port incorporated therein for the passage of primary liquid into said first chamber, said inlet port having a hydrophilic membrane incorporated therein and covered thereby, and an outlet port incorporated therein for the passage of liquid from said first chamber, said outlet port from said first chamber including a hydrophilic membrane incorporated therein and covered thereby for preventing the passage of air from said first chamber through said outlet port when said hydrophilic membrane is moistened;
a second chamber in said housing having an inlet port to said second chamber at the top thereof for the admission of secondary liquid therein and an outlet port from said second chamber for the passage of secondary liquid therefrom, said outlet port from said second chamber including a second hydrophilic membrane incorporated therein for preventing the passage of air therethrough; and
an air capturing pocket proximate said hydrophilic membrane covering said inlet port to said first chamber, said air capturing pocket comprising the area beneath said hydrophilic membrane covering said inlet port to said first chamber, the sides of said air capturing pocket being defined by the side walls of said first chamber proximate the top of said first chamber, said air capturing pocket being constructed and arranged for the reception of residual air within said first chamber proximate said hydrophilic membrane when said secondary liquid is dispensed into said second chamber whereby the flow of said primary liquid is interrupted for so long as the pressure of said secondary liquid is greater than that of said primary liquid.

2. A combined air barrier and liquid sequencing valve for the sequential administration of a primary liquid and a secondary liquid comprising:
a housing divided into two or more parallel chambers, a first chamber in said housing having an inlet port at the top thereof incorporated therein for the passage of primary liquid into said first chamber, said inlet port including a hydrophilic membrane incorporated therein and covered thereby, and an outlet port incorporated therein for the passage of said primary liquid from said first chamber, said outlet port from said first chamber includingg a hydrophilic membrane incorporated therein and covered thereby for preventing the passage of air from said first chamber through said outlet port when said hydrophilic membrane is moistened;

a second chamber in said housing having an inlet port for the admission of secondary liquid therein and an outlet port from said second chamber for the passage of secondary liquid therefrom, said outlet port from said second chamber including a second hydrophilic membrane incorporated therein for preventing the passage of air therethrough; and an air capturing pocket proximate said hydrophilic membrane covering said inlet port to said first chamber, said air capturing pocket comprising the area beneath said hydrophilic membrane covering said inlet port to said first chamber, the sides of said air capturing pocket being defined by the side walls of said first chamber, said air capturing pocket being constructed and arranged for the reception of residual air within said first chamber proximate said hydrophilic membrane when said secondary liquid is dispensed into said second chamber whereby the flow of said primary liquid is interrupted for so long as the pressure of said secondary liquid is greater than that of said primary liquid.

3. The combined air barrier and liquid sequencing valve defined in claim 1 or 2 and further including a reservoir incorporated therein for the reception of secondary liquid within said second chamber, said reservoir being constructed and arranged so as to overflow said secondary liquid into said first chamber thereby filling said first chamber and entrapping residual air within said air capturing pocket.

4. The valve defined in claim 1, wherein said inlet port to said first chamber is positioned proximate the top thereof and said inlet and outlet ports to said second chamber are respectively positioned proximate the top and side thereof.

5. The valve defined in claim 3, wherein said reservoir is integrally formed as a portion of said second chamber.

6. The valve defined in claim 1 or 2, wherein said first chamber further includes a closable air vent.

7. The valve defined in claim 6, wherein said air vent is covered by a hydrophobic membrane.

8. The valve defined in claim 1 or 3 wherein said air capturing pocket comprises a raised tubular portion incorporated in said first chamber, said hydrophilic membrane being incorporated in said raised tubular portion whereby air may be entrapped within said raised tubular portion during dispensing of secondary liquid due to the relatively greater partial pressure of said secondary liquid as compared to the partial pressure of said primary liquid thereby resulting in a greater partial pressure against the ventral surface of said hydrophilic membrane as opposed to the dorsal surface.

9. The combined air barrier and liquid sequencing valve defined in claim 1 or 2 wherein said second chamber further includes a closable air vent.

10. The combined air barrier and liquid sequencing valve defined in claim 9 wherein said air vent is positioned proximate the top of said housing and is covered by a hydrophobic membrane thereby preventing the passage of liquid therefrom.

11. The valve defined in claim 1 or 2 wherein said second chamber further comprises a reservoir incorporated therein, said reservoir comprising a hydrophilic membrane disposed across and selectively sealing said second chamber below said outlet, said hydrophilic membrane constructed and arranged to direct a portion of said secondary liquid into said first chamber until said first chamber is substantially filled, whereby said primary liquid flow is halted and said secondary liquid may pass through said outlet ports of said first and second chambers.

* * * * *